(12) United States Patent
Liu et al.

(10) Patent No.: US 10,465,062 B2
(45) Date of Patent: Nov. 5, 2019

(54) HIGH THERMAL STABILITY MELAMINE OCTAMOLYBDATE AND USE THEREOF AS A SMOKE SUPPRESSANT IN POLYMER COMPOSITIONS

(71) Applicant: J.M. Huber Corporation, Atlanta, GA (US)

(72) Inventors: Yue Liu, Marietta, GA (US); Aleksey Isarov, Kennesaw, GA (US); David Dwayne Temples, Calhoun, GA (US); David Stanley Reece, Calhoun, GA (US); Mitchell Lee Pierce, Fairmount, GA (US)

(73) Assignee: J.M. Huber Corporation, Atlanta, GA (US)

( * ) Notice: Subject to any disclaimer, the term of this patent is extended or adjusted under 35 U.S.C. 154(b) by 78 days.

(21) Appl. No.: 15/834,174

(22) Filed: Dec. 7, 2017

(65) Prior Publication Data

US 2018/0171107 A1    Jun. 21, 2018

Related U.S. Application Data

(60) Provisional application No. 62/435,937, filed on Dec. 19, 2016.

(51) Int. Cl.
| | | |
|---|---|---|
| *C08K 5/3492* | (2006.01) |
| *C07D 251/56* | (2006.01) |
| *C08K 3/22* | (2006.01) |
| *C07D 251/54* | (2006.01) |
| *C07D 251/70* | (2006.01) |

(52) U.S. Cl.
CPC ........ *C08K 5/34922* (2013.01); *C07D 251/54* (2013.01); *C07D 251/56* (2013.01); *C07D 251/70* (2013.01); *C08K 3/22* (2013.01); *C08K 2003/2224* (2013.01); *C08K 2003/2227* (2013.01)

(58) Field of Classification Search
None
See application file for complete search history.

(56) References Cited

U.S. PATENT DOCUMENTS

| | | | |
|---|---|---|---|
| 4,153,792 A | 5/1979 | Kroenke | |
| 4,217,292 A | 8/1980 | Kroenke | |
| 5,954,857 A * | 9/1999 | Rudloff | .................. C22C 29/00 75/228 |
| 6,217,797 B1 | 4/2001 | Day | |
| 6,355,277 B1 | 3/2002 | Day et al. | |
| 6,797,760 B1 | 9/2004 | Ebrahimian et al. | |
| 7,589,198 B2 * | 9/2009 | Tjioe | .................... C07D 251/60 544/203 |
| 8,070,990 B2 | 12/2011 | Ho et al. | |
| 8,277,703 B2 | 10/2012 | Walker et al. | |
| 2006/0084733 A1 | 4/2006 | O'Brien et al. | |
| 2011/0263773 A1* | 10/2011 | Walker | ..................... C08K 3/24 524/405 |

FOREIGN PATENT DOCUMENTS

WO    WO 2008/054818    5/2008

OTHER PUBLICATIONS

Kroenke et al, Inorganic Chemistry, vol. 22, No. 17, 1983 2413.*
International Search Report and the Written Opinion of the International Searching Authority in PCT/US2017/065043 dated Feb. 5, 2018, 14 pages.

* cited by examiner

*Primary Examiner* — Robert T Butcher
(74) *Attorney, Agent, or Firm* — Merchant & Gould P.C.

(57) ABSTRACT

Processes for producing melamine octamolybdates having high thermal stability include a step of reacting molybdenum trioxide and melamine in an acidic aqueous system at a pH of less than or equal to about 4 to form a slurry of the melamine octamolybdate. The resulting melamine octamolybdate can be characterized by a decomposition onset temperature (or a temperature at a weight loss of 1%, or a temperature at a weight loss of 2%) on a thermogravimetric analysis curve of greater than 300° C., and is useful in polymer compositions as a smoke suppressant.

20 Claims, 3 Drawing Sheets

HIGH THERMAL STABILITY MELAMINE OCTAMOLYBDATE AND USE THEREOF AS A SMOKE SUPPRESSANT IN POLYMER COMPOSITIONS

REFERENCE TO RELATED APPLICATION

This application claims the benefit of U.S. Provisional Application Ser. No. 62/435,937, filed on Dec. 19, 2016, the disclosure of which is incorporated herein by reference in its entirety.

BACKGROUND OF THE INVENTION

The present invention is directed generally to smoke suppressants that can be used in polymer compositions, and more particularly, to smoke suppressants having improved thermal stability for processing or end-use at elevated temperatures.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Processes for producing melamine octamolybdates having high thermal stability are disclosed and described herein. One such process for producing the melamine octamolybdate can comprise reacting molybdenum trioxide ($MoO_3$) and melamine in an acidic aqueous system at a pH of less than or equal to about 4 to form a slurry of the melamine octamolybdate. The resulting melamine octamolybdate can be characterized by a decomposition onset temperature (or a temperature at a weight loss of 1%, or a temperature at a weight loss of 2%) on a TGA (thermogravimetric analysis) curve in a range from about 300° C. to about 500° C., such as from about 325° C. to about 425° C., or from about 350° C. to about 390° C.

Melamine octamolybdates and supported melamine octamolybdates with high thermal stability also are disclosed and described herein. The supported melamine octamolybdates can contain various core materials, such as silica, alumina, alumina trihydrate, talc, calcium carbonate, clay, zinc oxide, zinc borate, or calcium borate, and this includes combinations of more than one core material.

Polymer compositions also are provided herein, and such compositions can comprise a polymer and any of the melamine octamolybdates or supported melamine octamolybdates disclosed herein (e.g., produced by any of the process disclosed herein). Generally, the weight ratio of polymer:melamine octamolybdate (or supported melamine octamolybdate) ranges from about 100:1 to about 100:40, or from about 100:5 to about 100:20. In these polymer compositions, the melamine octamolybdate component can act as a smoke suppressant.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated and can be interchanged, with or without explicit description of the particular combination. Accordingly, unless explicitly recited otherwise, any aspect or feature disclosed herein can be combined to describe inventive designs, compositions, processes, or methods consistent with the present disclosure.

While compositions and methods are described herein in terms of "comprising" various components or steps, the compositions and methods can also "consist essentially of" or "consist of" the various components or steps, unless stated otherwise. For example, polymer compositions consistent with aspects of the present invention can comprise; alternatively, can consist essentially of; or alternatively, can consist of; (1) a polymer, and (2) a melamine octamolybdate having high thermal stability.

The terms "a," "an," and "the" are intended to include plural alternatives, e.g., at least one, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, and so forth.

The term "contacting" is used herein to refer to materials or components which can be blended, mixed, slurried, dissolved, reacted, treated, compounded, or otherwise contacted or combined in some other manner or by any suitable method. The materials or components can be contacted together in any order, in any manner, and for any length of time, unless otherwise specified.

Molybdenum trioxide ($MoO_3$) often can be referred to as molybdic trioxide, molybdenum (VI) oxide, and molybdic anhydride (or molybdic acid anhydride). As one of skill in the art would readily recognize, in an (acidic) aqueous environment, molybdenum trioxide can form molybdic acid and other species such as hydrates and molybdates. Thus, when the use of molybdenum trioxide in an aqueous mixture or acidic aqueous system is disclosed herein, this is meant to encompass any forms of molybdenum species or complexes that exist in the aqueous environment, whether molybdic acid, a hydrate, a molybdate, and the like, as well as combinations thereof.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications and patents, which might be used in connection with the presently described invention.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. As a representative example, the d50 particle size of the melamine octamolybdate can be in certain ranges in various aspects of this invention. By a disclosure that the d50 particle size can be in a range from about 1 to about 10 µm, the intent is to recite that the d50 can be any particle size within the range and, for example, can be equal to about 1, about 2, about 3, about 4, about 5, about 6, about 7, about 8, about 9, or about 10 µm. Additionally, the d50 particle size can be within any range from about 1 to about 10 µm (for example, from about 2 to about 6 µm), and this also includes any combination of ranges between about 1 and about 10 µm (for example, the d50 particle size can be in a range from about 1 to about 4 µm or from about 6 to about 8 µm). Likewise, all other ranges disclosed herein should be interpreted in a manner similar to this example.

The term "about" means that amounts, sizes, formulations, parameters, and other quantities and characteristics are not and need not be exact, but may be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

DETAILED DESCRIPTION OF THE INVENTION

Disclosed herein are melamine octamolybdate smoke suppressants having improved thermal stability, methods for producing the melamine octamolybdates, and polymer compositions and articles of manufacture containing the melamine octamolybdates.

These melamine octamolybdate smoke suppressants, unexpectedly, have excellent thermal stability at elevated temperatures. Beneficially, such melamine octamolybdate smoke suppressants can be used in polymer compositions that are subjected to high temperature processing (e.g., extrusion), or where the end-use application for the polymer composition requires long-term stability of the smoke suppressant, particularly at elevated temperatures.

Processes for Producing Melamine Octamolybdate

Various processes for producing melamine octamolybdate, which has high thermal stability, are provided herein. One such method for producing melamine octamolybdate can comprise (or consist essentially of, or consist of) reacting molybdenum trioxide ($MoO_3$) and melamine in an acidic aqueous system at a pH of less than or equal to about 4 to form a slurry of the melamine octamolybdate. The melamine octamolybdate can be characterized by a decomposition onset temperature (or a temperature at a weight loss of 1%, or a temperature at a weight loss of 2%) on a TGA (thermogravimetric analysis) curve in a range from about 300° C. to about 500° C.

Generally, the features of any of the processes disclosed herein (e.g., the melamine octamolybdate, the molybdenum trioxide ($MoO_3$), the melamine, the acidic aqueous system, the pH, the decomposition onset temperature, the temperature at a weight loss of 1%, the temperature at a weight loss of 2%, and the conditions under which the molybdenum trioxide and melamine are contacted or reacted, among others) are independently described herein, and these features can be combined in any combination to further describe the disclosed processes. Moreover, other process steps can be conducted before, during, and/or after any of the steps listed in the disclosed processes, unless stated otherwise. Additionally, melamine octamolybdates produced in accordance with any of the disclosed processes are within the scope of this disclosure and are encompassed herein.

The slurry of the melamine octamolybdate can be formed at a variety of temperatures, pressures, and time periods. Typical temperatures often fall within a range from about 60° C. to about 95° C., such as from about 70° C. to about 95° C., from about 75° C. to about 90° C., or from about 80° C. to about 90° C. In these and other aspects, these temperature ranges also are meant to encompass circumstances where the melamine octamolybdate is formed at a series of different temperatures, instead of at a single fixed temperature, falling within the respective ranges. The pressure at which the slurry of the melamine octamolybdate is formed is not particularly limited, but can be at an elevated pressure (e.g., from about 5 psig to about 100 psig), at atmospheric pressure, or at any suitable sub-atmospheric pressure. In some instances, the melamine octamolybdate is produced at atmospheric pressure, eliminating the need for pressurized vessels and their associated cost and complexity. The slurry of the melamine octamolybdate can be formed over a wide range of time periods, such as from about 30 min to about 24 hr, from about 1 hr to about 12 hr, or from about 90 min to about 6 hr, but is not limited solely to these time periods. Other appropriate temperature, pressure, and time ranges are readily apparent from this disclosure.

In the process for producing melamine octamolybdate —$(C_3H_7N_6)_4Mo_8O_{26}$— the molybdenum trioxide and the melamine can be contacted or reacted at a molar ratio of Mo:N that typically falls within a range from about 1:2 to about 1:4, based on the total amount of each reactant, and regardless of the order of addition or contacting of the reactants, or the addition method that is used. This ratio is also based on the total nitrogens in the melamine, whether the nitrogen is a ring nitrogen or not. As a skilled artisan would readily recognize, the molar ratio of Mo:N can vary as the reaction proceeds; therefore, the disclosed ranges of molar ratio encompass any molar ratio encountered during the reaction and formation of the slurry of the melamine octamolybdate. In further aspects of this invention, the ratio of Mo:N can be in a range from about 1:2 to about 1:4, from about 1:2 to about 2:7, from about 2:5 to about 1:4, from about 2:5 to about 2:7, or from about 3:8 to about 3:10. Other appropriate ranges for ratio of Mo:N, and whether excess molybdenum trioxide or melamine is present, are readily apparent from this disclosure. For instance, the molar ratio of Mo:N can be a stoichiometric ratio of about 1:3 (+/−10%), reflective of the resulting melamine octamolybdate having the formula, $(C_3H_7N_6)_4Mo_8O_{26}$.

In one aspect, the acidic aqueous system has a pH in a range from about 1 to about 4, from about 2 to about 4, or from about 3 to about 4, while in another aspect, the acidic aqueous system has a pH in a range from about 1.5 to 4, from about 1.5 to about 3.5, from about 1 to about 3, from about 1.5 to about 2.5, or from about 2 to about 3. As a skilled artisan would readily recognize, the pH of the acidic aqueous system, and the pH at which the slurry of the melamine octamolybdate is formed, can vary as the reactions proceeds; therefore, the disclosed ranges of pH encompass any pH encountered during the reaction and formation of the slurry of the melamine octamolybdate. Other appropriate ranges for the pH are readily apparent from this disclosure.

The order and manner of contacting the molybdenum trioxide and melamine is not particularly limited. For instance, in one aspect of this invention, the molybdenum trioxide can be contacted with an aqueous mixture of the melamine (solution, slurry), while in another aspect, the melamine can be contacted with an aqueous slurry of the molybdenum trioxide.

Yet, in another aspect, the reacting of the molybdenum trioxide and melamine can comprise adding an aqueous mixture of the melamine to a saturated aqueous mixture (solution/slurry) of the molybdenum trioxide having a pH of less than or equal to about 4. Accordingly, illustrative and non-limiting ranges for the pH of the saturated aqueous mixture can include the following ranges: from about 1 to about 4, from about 2 to about 4, from about 3 to about 4, from about 1.5 to 4, from about 1.5 to about 3.5, from about 1 to about 3, from about 1.5 to about 2.5, or from about 2 to about 3. As a skilled artisan would readily recognize, the pH of the saturated aqueous mixture can vary as the reaction proceeds and as the slurry of the melamine octamolybdate is formed; therefore, the disclosed ranges of pH encompass any pH encountered during the reaction and formation of the slurry of the melamine octamolybdate. Other appropriate ranges for the pH are readily apparent from this disclosure. As an example, the pH of the saturated aqueous mixture of the molybdenum trioxide can be equal to about 2 prior to the addition of the melamine (which has a basic pH), while the pH of the acidic aqueous system after all of the melamine has been added often can fall within a pH range of 3.5 to 4.

In this aspect of the invention, the aqueous mixture of the melamine (solution, slurry) can be added slowly to the saturated aqueous mixture (solution/slurry) of the molybdenum trioxide over any suitable period of time. Often, but not limited thereto, this time period ranges from about 30 min to about 24 hr, from about 1 hr to about 12 hr, or from about 90 min to about 6 hr. Other appropriate ranges for the time period of contacting or reacting the aqueous mixture of the melamine with the saturated aqueous mixture of the molybdenum trioxide are readily apparent from this disclosure.

In some aspects, the d50 particle size (median particle size) of the molybdenum trioxide can be in a range from about 0.5 to about 20 μm, such as, for instance, from about 0.5 to about 6 μm, from about 1 to about 10 μm, from about 1 to about 6 μm, from about 1.6 to about 6 μm, or from about 1.6 to about 4 μm. Additionally or alternatively, the d50 particle size (median particle size) of the melamine can be in a range from about 10 to about 150 μm, from about 20 to about 120 μm, or from about 40 to about 110 μm, and the d90 particle size of the melamine can be in a range from about 70 to about 250 μm, from about 80 to about 200 μm, or from about 90 to about 175 μm. Other appropriate particle sizes for the molybdenum trioxide and the melamine are readily apparent from this disclosure.

In the process for producing melamine octamolybdate, the molar yield of the melamine octamolybdate, based on the limiting reactant (molybdenum trioxide or melamine), often is greater than 90%. Molar yields in the range from about 90 to 100%, from about 95 to 100%, from about 90 to about 99%, from about 92 to about 99%, or from about 90 to about 96%, are contemplated in aspects of this invention.

Optionally the process for producing melamine octamolybdate can further comprise a step of removing the melamine octamolybdate from the slurry using any suitable separations technique. For example, filtration or centrifugation can be used, as well as a combination of these techniques.

Optionally, the process for producing melamine octamolybdate can further comprise a step of drying the melamine octamolybdate using any suitable drying conditions. For example, drying temperatures ranging from about 50° C. to about 200° C., or from about 100° C. to about 150° C., can be used, and the drying can be conducted at atmospheric pressure or any suitable sub-atmospheric pressure, e.g., less than about 150 Torr, or less than about 50 Torr.

If desired, the process for producing melamine octamolybdate can comprise contacting or reacting the melamine and the molybdenum trioxide in the presence of a core material, thereby forming a supported melamine octamolybdate. This can increase the effective surface area of the melamine octamolybdate material, and its effectiveness as a smoke suppressant, such as disclosed in U.S. Pat. Nos. 8,070,990 and 8,277,703, incorporated herein by reference in their entirety. Illustrative and non-limiting examples of core materials can include silica, alumina, alumina trihydrate, talc, calcium carbonate, clay, zinc oxide, zinc borate, or calcium borate, and the like, as well as combinations of more than one of these core materials.

Melamine Octamolybdate Smoke Suppressants

Consistent with aspects of the present invention, the melamine octamolybdate described herein (or the melamine octamolybdate produced in accordance with any of the processes disclosed herein) can have unexpectedly high thermal stability, for instance, as characterized by a decomposition onset temperature on a TGA (thermogravimetric analysis) curve that falls within a range from about 300° C. to about 500° C.; additionally or alternatively, characterized by a temperature at a weight loss of 1% that falls within a range from about 300° C. to about 500° C.; or additionally or alternatively, characterized by a temperature at a weight loss of 2% that falls within a range from about 300° C. to about 500° C.

In one aspect, the melamine octamolybdate can be characterized by a decomposition onset temperature (or a temperature at a weight loss of 1%, or a temperature at a weight loss of 2%) on a TGA curve in a range from about 325° C. to about 475° C. In another aspect, the melamine octamolybdate can be characterized by a decomposition onset temperature (or a temperature at a weight loss of 1%, or a temperature at a weight loss of 2%) on a TGA curve in a range from about 325° C. to about 425° C. In yet another aspect, the melamine octamolybdate can be characterized by a decomposition onset temperature (or a temperature at a weight loss of 1%, or a temperature at a weight loss of 2%) on a TGA curve in a range from about 330° C. to about 400° C. In still another aspect, the melamine octamolybdate can be characterized by a decomposition onset temperature (or a temperature at a weight loss of 1%, or a temperature at a weight loss of 2%) on a TGA curve in a range from about 350° C. to about 390° C. Other appropriate ranges for the decomposition onset temperature (or for the temperature at a weight loss of 1%, or for the temperature at a weight loss of 2%) of the melamine octamolybdate are readily apparent from this disclosure.

While not being limited thereto, the melamine octamolybdate can be further characterized by a d50 particle size (median particle size) in a range from about 0.5 to about 20 μm, such as, for instance, from about 0.5 to about 6 μm, from about 1 to about 10 μm, from about 1 to about 6 μm, from about 2 to about 12 μm, or from about 2 to about 4 μm. Other appropriate particle sizes for the melamine octamolybdate are readily apparent from this disclosure.

Consistent with aspects of the present invention, the supported melamine octamolybdate described herein (or the supported melamine octamolybdate produced in accordance with any of the processes disclosed herein) can have unexpectedly high thermal stability, for instance, as characterized by a decomposition onset temperature (or a temperature at a weight loss of 1%, or a temperature at a weight loss of 2%) on a TGA (thermogravimetric analysis) curve that falls within a range from about 300° C. to about 500° C. In one aspect, the supported melamine octamolybdate can be characterized by a decomposition onset temperature (or a temperature at a weight loss of 1%, or a temperature at a weight loss of 2%) on a TGA curve in a range from about 325° C. to about 475° C. In another aspect, the supported melamine octamolybdate can be characterized by a decomposition onset temperature (or a temperature at a weight loss of 1%, or a temperature at a weight loss of 2%) on a TGA curve in a range from about 325° C. to about 425° C. In yet another aspect, the supported melamine octamolybdate can be characterized by a decomposition onset temperature (or a temperature at a weight loss of 1%, or a temperature at a weight loss of 2%) on a TGA curve in a range from about 330° C. to about 400° C. In still another aspect, the supported melamine octamolybdate can be characterized by a decomposition onset temperature (or a temperature at a weight loss of 1%, or a temperature at a weight loss of 2%) on a TGA curve in a range from about 350° C. to about 390° C. Other appropriate ranges for the decomposition onset temperature (or for the temperature at a weight loss of 1%, or for the temperature at a weight loss of 2%) of the supported melamine octamolybdate are readily apparent from this disclosure.

The supported melamine octamolybdate can comprise a melamine octamolybdate supported on a core material, for instance, any high thermal stability melamine octamolybdate disclosed herein supported on any core material disclosed herein. Illustrative and non-limiting examples of core materials can include silica, alumina, alumina trihydrate, talc, calcium carbonate, clay, zinc oxide, zinc borate, or calcium borate, and the like, as well as combinations of more than one of these core materials.

Melamine Octamolybdate Smoke Suppressant Compositions

This invention is also directed to, and encompasses, any compositions, formulations, composites, and articles of manufacture that contain any of the high thermal stability, melamine octamolybdate smoke suppressants disclosed herein (and their respective characteristics or features, such as the decomposition onset temperature, the median particle size, the use of a core material, and so forth). In a particular aspect of this invention, a polymer composition is disclosed, and in this aspect, the polymer composition can comprise any suitable polymer (one or more than one) and any of the melamine octamolybdates or supported melamine octamolybdates disclosed herein.

In one aspect, the polymer in the polymer composition can comprise a thermoplastic polymer, while in another aspect, the polymer can comprise a thermoset polymer. In another aspect, the polymer can comprise, either singly or in any combination, a polyvinylidene chloride (PVDC), a polyvinyl chloride (PVC), a chlorinated polyvinyl chloride (CPVC), a polyvinylidene fluoride (PVDF), a polytetrafluoroethylene (PTFE), and/or an ethylene chlorotrifluoroethylene (ECTFE). In yet another aspect, the polymer can comprise a plasticized or non-plasticized PVC. In still another aspect, the polymer can comprise a rigid PVC, or alternatively, the polymer can comprise a flexible PVC. Generally, rigid PVC may be referred to as non-plasticized PVC, while flexible PVC may be referred to as plasticized PVC.

As one of skill in the art would readily recognize, PVDC can be referred to as polyvinylidene chloride, but also can be referred to as poly(vinylidene chloride). Likewise, PVC can be referred to as polyvinyl chloride, but also can be referred to as poly(vinyl chloride).

While not being limited thereto, the weight ratio of polymer:melamine octamolybdate (or polymer:supported melamine octamolybdate) often can range from about 100:1 to about 100:40 in the polymer composition. Illustrative and non-limiting weight ratios of polymer:melamine octamolybdate (or polymer:supported melamine octamolybdate) can include the following ranges: from about 100:1 to about 100:20, from about 100:1 to about 100:5, from about 100:5 to about 100:40, from about 100:5 to about 100:30, from about 100:5 to about 100:20, from about 100:2 to about 100:25, or from about 100:2 to about 100:15. Other appropriate ranges for the weight ratio of polymer:melamine octamolybdate (or polymer:supported melamine octamolybdate) are readily apparent from this disclosure.

Optionally, the polymer composition can further comprise any suitable inorganic flame retardant, non-limiting examples of which can include aluminum trihydrate and magnesium hydroxide, as well as combinations thereof. Thus, in one aspect of this invention, the polymer composition can further comprise aluminum trihydrate, while in another aspect, the polymer composition can further comprise magnesium hydroxide.

Beneficially, the use of the melamine octamolybdate disclosed herein in a polymer composition can reduce the amount of smoke generated when the polymer composition is subjected to fire, flames, or burning. That is, the melamine octamolybdate disclosed herein can be used as a smoke suppressant.

For instance, the polymer composition can have a normalized total smoke in a range from about 30 to about 50 $m^2/m^2$ per gram of the polymer composition. The units of total smoke density are $m^2/m^2$, and the total smoke density is normalized by dividing the total smoke by the sample size of the polymer composition (in grams). In particular aspects of this invention, the polymer composition can have a normalized total smoke in a range from about 32 to about 48, from about 35 to about 50, or from about 35 to about 45, m²/m² per gram of the polymer composition.

While smoke suppressant performance (e.g., lower values of the normalized total smoke) can be an important property for the polymer composition, there are other considerations for the selection of a particular smoke suppressant, such as compatibility of the smoke suppressant with the polymer, the processability and flow characteristics of the polymer composition containing the smoke suppressant, the thermal stability of the smoke suppressant (for high temperature processing and/or high temperature end-use applications), and the cost of the smoke suppressant, among others. Thus, the melamine octamolybdate does not have to be the best smoke suppressant to be the material of choice; a combination of properties, as one of skill in the art would readily recognize, will determine the most suitable smoke suppressant for the particular end-use application. For instance, if high temperature thermal processing of the polymer composition (containing the smoke suppressant) is a requirement, the melamine octamolybdate disclosed herein may be the material of choice, even though another smoke suppressant may provide lower values of normalized total smoke.

Accordingly, in an aspect of this invention, the polymer composition (containing melamine octamolybdate) can have a normalized total smoke that is less than that (or within about 5 m²/m² per gram, or within about 2 m²/m² per gram) of a polymer composition containing ammonium octamolybdate, under the same processing conditions and with the same amount of smoke suppressant. Thus, the melamine octamolybdate may have better smoke suppressant properties than ammonium octamolybdate, or the melamine octamolybdate may have smoke suppressant properties that are comparable to ammonium octamolybdate, but may be used in the particular end-use application due to a better combination of properties (e.g., high temperature thermal stability).

Additionally or alternatively, the polymer composition (containing melamine octamolybdate) can have a normalized total smoke that is less than that (or within about 5 m²/m² per gram, or within about 2 m²/m² per gram) of a polymer composition containing a zinc molybdate/magnesium hydroxide complex, under the same processing conditions and with the same amount of smoke suppressant. Thus, the melamine octamolybdate may have better smoke suppressant properties than the zinc molybdate/magnesium hydroxide complex, or the melamine octamolybdate may have smoke suppressant properties that are comparable to the zinc molybdate/magnesium hydroxide complex, but may be used in the particular end-use application due to a better combination of properties (e.g., high temperature thermal stability).

Articles of manufacture can be formed from and/or can comprise any of the polymer compositions described herein. In an aspect, the article of manufacture can comprise a (polymeric) sheet or film. In another aspect, the article of manufacture can comprise a tube or pipe. In yet another aspect, the article of manufacture can comprise a wire or cable. For instance, the polymer composition can be used as a wire and cable insulation layer or used in wire and cable jacketing. Other appropriate articles of manufacture and end-use applications are readily apparent from this disclosure.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

The d50 particles size, or median particle size, refers to the particle size for which 50% of the sample has a smaller size and 50% of the sample has a larger size. Particle size measurements can be determined by laser diffraction in accordance with ISO 13320.

TGA measurements were performed on a TA Instrument TGA Q-500. A 5 mg to 20 mg sample was placed in a platinum pan and loaded onto a microbalance inside the TGA furnace. The sample was initially equilibrated at 30° C. with a $N_2$ flow rate of 60 mL/min, and the sample heated to 1000° C. at a temperature ramping rate of 20° C./min. Weight loss was recorded during the process. The decomposition onset temperature referred to herein is an "extrapolated" onset temperature, which is a reproducible temperature calculation described in ASTM E2550-11. The "extrapolated" onset temperature, as the name implies, was determined by calculating the point of intersection of two straight extrapolated lines: one was extrapolated from the initial baseline when there was no weight loss, and the other was the first tangent of the initial weight loss trending line. From the TGA data, the temperatures at a weight loss of 1 wt. % and a weight loss of 2 wt. % also were determined.

The normalized total smoke was calculated by dividing the total smoke density (m²/m²) by the sample size of the polymer composition (in grams). The total smoke density was determined on PVC composition specimens using a cone calorimeter (DEATAK Model CC-2) in accordance with ASTM E1354 and ISO 5660. The dimensions of the test specimens were 4"×4"×30 mils. The DEATAK model CC-2 cone calorimeter external heat flux was set to 80 kW/m², and the test specimens were subjected to these conditions for 5 min. Pre-ignition and post-ignition smoke production as specified in ISO 5660 were summed, thus yielding total smoke density. The total smoke density's for three specimens per sample composition were averaged and normalized to the average weight (in grams) of the three specimens. Total smoke density and normalized total smoke density were recorded.

Examples 1-3

Melamine octamolybdate was prepared in the presence of hydrochloric acid as follows for Example 1. A hydrochloric acid solution was prepared by mixing 11.6 g of hydrochloric acid (37%) with 50 mL of water. 20 grams of ammonium dimolybdate were dissolved in the aqueous hydrochloric acid solution at a pH of 1.5. Separately, 7.4 grams of melamine (d50=80 μm, d90=130 μm) were dissolved in 200 mL of water. Both solutions were heated to a temperature of 90° C. The second solution was added to the first solution at 90° C. at atmospheric pressure. A precipitate formed rapidly. The reaction mixture was maintained at 90° C. with vigorous agitation for 4 hr at a pH of below 3, and thereafter filtered hot through Pannevis filter fabric that was supported on a Buchner funnel. A white solid was separated and washed five times with 250 mL of water and once with 100 mL of ethanol. The solid was dried for about 12 hr at 110° C., and the final weight was 23.6 grams. The reaction for Example 1 is represented by reaction scheme (1) below.

$$4(NH_4)_2Mo_2O_7 + 4C_3H_6N_6 + 8HCl \Rightarrow (C_3H_7N_6)_4Mo_8O_{26} + 8NH_4Cl + 2H_2O \qquad (1)$$

Melamine octamolybdate was prepared by the reaction of molybdic acid with melamine in Example 2. Molybdenum trioxide (228.3 grams, 1.58 moles, d50=4 μm, d90=20 μm) was added while stirring to 600 mL of water at 85° C. with the pH equal to about 2. Melamine (100 grams, 0.792 moles, d50=80 μm, d90=130 μm) was added while stirring to 2000 mL of water at 85° C. with the pH equal to about 8. The melamine solution was added dropwise through a peristaltic pump to the molybdic acid mixture at 90° C. over a time period of 2 hr at atmospheric pressure; the pH of the mixture was below 4 during the addition process. The reaction mixture was maintained at 90° C. with vigorous agitation for 4 hr. Then, the mixture was dried for about 12 hr at 110° C., and the final weight was 328.3 grams. The reaction for Example 2 is represented by reaction scheme (2) below.

$$8MoO_3 + 4C_3H_6N_6 + 2H_2O \Rightarrow (C_3H_7N_6)_4Mo_8O_{26} \tag{2}$$

Example 3 was a melamine octamolybdate commercially available under the grade designation of CHARMAX LS-MOM.

Table I summarizes the decomposition onset temperature, the temperature at a weight loss of 1%, and the temperature at a weight loss of 2%, determined using TGA (thermogravimetric analysis), for the melamine octamolybdates of Examples 1-3. Unexpectedly, and beneficially, the melamine octamolybdate of Example 2 had a decomposition onset temperature, a temperature at a weight loss of 1%, and a temperature at a weight loss of 2%, that were greater than 350° C., indicating excellent thermal stability at elevated temperatures. In comparison, the melamine octamolybdate of Example 3 had a decomposition onset temperature, a temperature at a weight loss of 1%, and a temperature at a weight loss of 2%, that were less than 250° C., while the melamine octamolybdate of Example 1 had a decomposition onset temperature, a temperature at a weight loss of 1%, and a temperature at a weight loss of 2%, that were less than 160° C.

Figure 1:
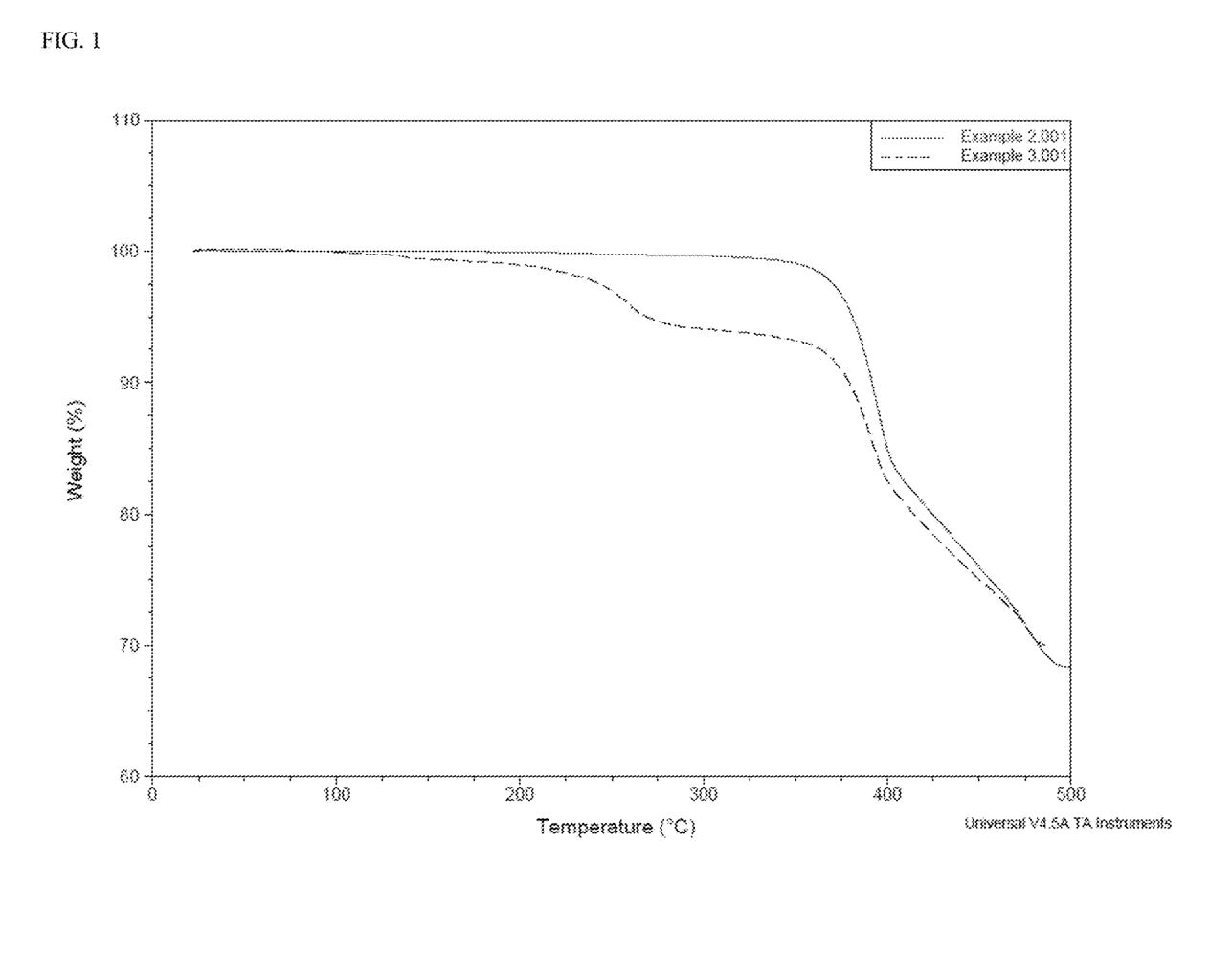
FIG. 1 presents thermogravimetric analysis (TGA) plots of the melamine octamolybdates of Example 2 and Example 3.

FIG. 1 illustrates the TGA plots of the melamine octamolybdates of Example 2 and Example 3, and demonstrates the significant differences in thermal stability in the 200-400° C. range.

Examples 4-7

Rigid PVC polymer formulations were produced using various smoke suppressant additives at 6 phr (parts by weight per hundred parts of resin), as summarized in Table II. Example 4 used an ammonium molybdate (AOM), Example 5 used a zinc molybdate/magnesium hydroxide complex (MZM), Example 6 used the melamine octamolybdate of Example 2 (MOM), and Example 7 used Vertex 100 magnesium hydroxide (V100) at 14 phr (no calcium carbonate was used).

A rigid PVC masterbatch was prepared using a 10-L high shear Henschel mixer. Axiall 1091 PVC resin was added to the Henschel mixer and mixed at high rpm (3600) until the PVC resin reached 70° C. At the same time, a TOTM plasticizer was heated on a hot plate to reach 70° C. When the PVC resin and plasticizer reached 70° C., the plasticizer was added to the Henschel mixer containing the PVC resin. The PVC resin and plasticizer were mixed at high rpm (3600) until reaching 100° C. At that point, Hydral 710, Vertex 90 SF, Antimony Trioxide, and Stearic Acid were added to the Henschel mixer. The mixture was mixed at high rpm (3600) until reaching 125° C. Cooling water was then flowed through a cooling jacket of the Henschel mixer as the masterbatch mixed at low rpm (700). When the masterbatch reached 80° C., it was dumped and ready for compounding.

For Example 6, approximately 265 grams of the PVC masterbatch (PVC MB Axiall 1091) were combined with 20 grams of Optifil T calcium carbonate and 15 grams of the melamine octamolybdate of Example 2, and then blended for 1 min. This blend was fluxed in a 75-mL Brabender at 185° C., then mixed an additional 3 min. The resulting material was compression molded with an electrically heated hydraulic press at 190° C. Examples 4-5 and 7 were produced in a similar manner.

Figure 2:
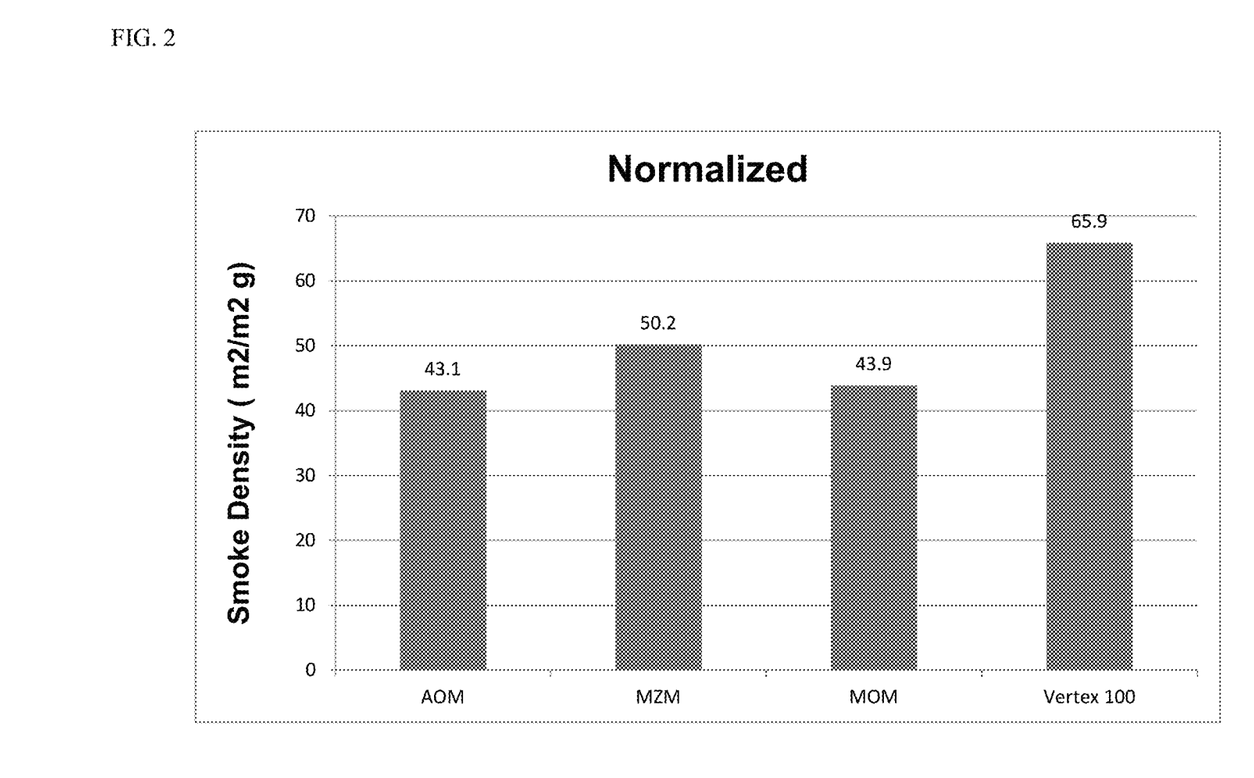
FIG. 2 presents a bar chart of the normalized total smoke for the rigid PVC polymer compositions of Examples 4-7, which contained 6 phr of different smoke suppressants.

FIG. 2 is a bar chart summarizing the normalized total smoke ($m^2/m^2$ per gram of the polymer composition sample) for the rigid PVC polymer compositions of Examples 4-7. As shown in FIG. 2, the MOM composition (Example 6) unexpectedly had low smoke density, and was comparable to the AOM composition (Example 4). The MOM composition (Example 6) outperformed the MZM and Vertex 100 compositions in terms of smoke suppression.

Examples 8-11

Flexible PVC polymer formulations were produced using various smoke suppressant additives at 15 phr (parts by weight per hundred parts of resin), in a similar manner to Examples 4-7. Example 8 used the ammonium molybdate (AOM), Example 9 used the zinc molybdate/magnesium hydroxide complex (MZM), Example 10 used the melamine octamolybdate of Example 2 (MOM), and Example 11 used the Vertex 100 magnesium hydroxide (V100).

A flexible PVC masterbatch was prepared using a 10-L high shear Henschel mixer (see Table III for a summary of masterbatch ingredients). Georgia Gulf 5415 PVC resin was added to the Henschel mixer and mixed at high rpm (3600) until the PVC resin reached 70° C. At the same time, the TOTM plasticizer was heated on a hot plate and allowed to reach 70° C. When the PVC resin and plasticizer reached 70° C., the plasticizer was added to the Henschel mixer containing the PVC resin. The PVC resin and plasticizer were allowed to mix at high rpm (3600) until reaching 100° C. At that point, the Hydral 710, Vertex 90 SF, Antimony Trioxide, Stabilizer, and Stearic Acid were added to the Henschel mixer. The mixture was mixed at high rpm (3600) until reaching 125° C. Cooling water was then flowed through a cooling jacket of the Henschel mixer as the masterbatch mixed at low rpm (700). When the masterbatch reached 80° C., it was dumped and ready for compounding.

For Example 10, approximately 373.7 grams of the PVC masterbatch were combined with 26.3 grams of the melamine octamolybdate of Example 2, and then blended for 1 min in a Hobart mixer. The flexible PVC specimens were fused using a 75-mL Brabender Plasti-Corder DigiSystem equipped with Type 6 roller blades (3:2 speed ratio). The fusion process parameters included a mixing temperature of 165° C. and a mixing time of 5 min. The fused samples were compression molded with an electrically heated hydraulic Carver press at 385° F. Examples 8-9 and 11 were produced in a similar manner.

Figure 3:
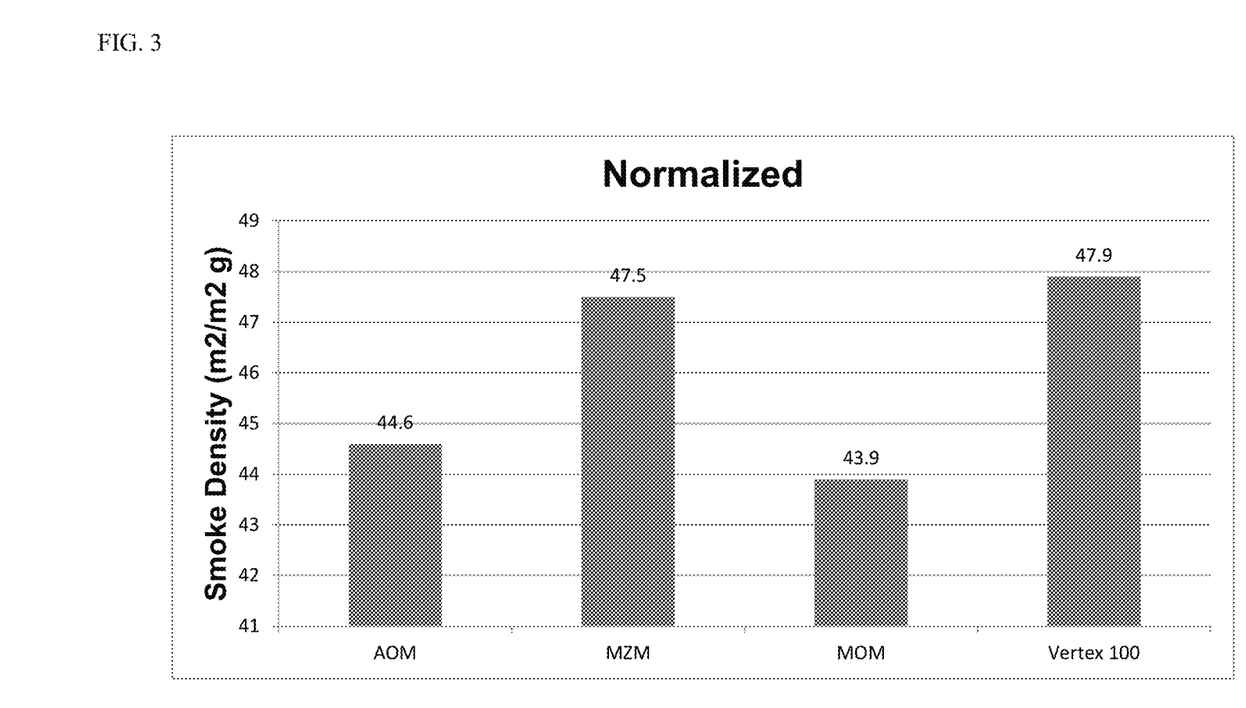
FIG. 3 presents a bar chart of the normalized total smoke for the flexible PVC polymer compositions of Examples 8-11, which contained 15 phr of different smoke suppressants.

FIG. 3 is a bar chart summarizing the normalized total smoke ($m^2/m^2$ per gram of the polymer composition sample) for the flexible PVC polymer compositions of Examples 8-11. As shown in FIG. 3, the MOM composition (Example 10) unexpectedly had the best smoke suppression, and was superior to the AOM composition (Example 8), the MZM composition (Example 9) and the Vertex 100 composition (Example 11).

Example 12

In Example 12, melamine octamolybdate was prepared by the reaction of molybdic acid with melamine in a manner similar to Example 2. Molybdenum trioxide (456 grams, 3.17 moles) was added while stirring to 900 mL of water at 85° C. with the pH equal to about 2. Melamine (200 grams, 1.59 moles) was added while stirring to 4500 mL of water at 85° C. with the pH equal to at about 8. The melamine solution was added dropwise through a peristaltic pump to the molybdic acid mixture at 90° C. over a time period of 2 hr at atmospheric pressure; the pH of the mixture was below 4 during the addition process. The reaction mixture was maintained at 90° C. with vigorous agitation for 4 hr. Then, the mixture was dried for about 12 hr at 110° C., and the final weight was 644.3 grams.

Unexpectedly, and beneficially, the melamine octamolybdate of Example 12 had excellent thermal stability: a decomposition onset temperature equal to 375.1° C., a temperature at a weight loss of 1% equal to 351.4° C., and a temperature at a weight loss of 2% equal to 366.4° C.

TABLE I

Thermal Stability Comparison of the Melamine Octamolybdates of Examples 1-3

| Example | Decomposition Onset Temperature (° C.) | Temperature at 1% Weight Loss (° C.) | Temperature at 2% Weight Loss (° C.) |
|---|---|---|---|
| 1 | 158.4 | 137.6 | 154.3 |
| 2 | 373.2 | 352.6 | 367.0 |
| 3 | 219.2 | 197.9 | 234.2 |

TABLE II

Examples 4-7 - Smoke Suppressant Polymer Formulations (all amounts are in phr)

| | Example | | | |
|---|---|---|---|---|
| | 4 | 5 | 6 | 7 |
| | | Smoke Suppressant | | |
| | AOM | MZM | MOM | V100 |
| PVC MB Axiall 1091 | 106.7 | 106.7 | 106.7 | 106.7 |
| CaCO$_3$ | 8.0 | 8.0 | 8.0 | |
| AOM | 6.0 | | | |
| MZM | | 6.0 | | |
| MOM | | | 6.0 | |
| V100 | | | | 14.0 |
| Total | 120.7 | 120.7 | 120.7 | 120.7 |

TABLE III

Masterbatch Ingredients in Examples 8-11

| Ingredient | Description |
|---|---|
| PVC Resin | Georgia Gulf 5415 (K70) |
| Plasticizer | Aldrich - Trioctyl Trimellitate (TOTM) |
| Stabilizer | Chemson - Naftosafe PPK-2010 |
| Lubricant | PMC Corporation - Industrene B Stearic Acid |
| Sb$_2$O$_3$ | Youngsun & Essen Corporation - Alpha 2 Grade Antimony Trioxide |
| ATH | Huber Hydral 710 |
| MDH | Huber Vertex 90SF |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for producing melamine octamolybdate, the process comprising reacting molybdenum trioxide (MoO$_3$) and melamine in an acidic aqueous system at a pH of less than or equal to about 4 to form a slurry of the melamine octamolybdate; wherein the melamine octamolybdate is characterized by a decomposition onset temperature (or a temperature at a weight loss of 1%, or a temperature at a weight loss of 2%) on a TGA (thermogravimetric analysis) curve in a range from about 300° C. to about 500° C.

Aspect 2. The process defined in aspect 1, wherein the pH is in any suitable range, or in any range disclosed herein, e.g., from about 1 to about 4, from about 2 to about 4, from about 3 to about 4, from about 1.5 to 4, from about 1.5 to about 3.5, from about 1 to about 3, from about 1.5 to about 2.5, or from about 2 to about 3.

Aspect 3. The process defined in aspect 1 or 2, wherein the molybdenum trioxide and the melamine are contacted or reacted at a molar ratio of Mo:N in any suitable range, or in any range of Mo:N disclosed herein (total nitrogen), e.g., from about 1:2 to about 1:4, from about 1:2 to about 2:7, from about 2:5 to about 1:4, from about 2:5 to about 2:7, or from about 3:8 to about 3:10, based on the total amount of each reactant.

Aspect 4. The process defined in any one of the preceding aspects, wherein the slurry of the melamine octamolybdate is formed at a temperature in any suitable range, or in any range disclosed herein, e.g., from about 70° C. to about 95° C., from about 75° C. to about 90° C., or from about 80° C. to about 90° C.

Aspect 5. The process defined in any one of the preceding aspects, wherein the slurry of the melamine octamolybdate is formed at a pressure in any suitable range, or in any range disclosed herein, e.g., from about 5 psig to about 100 psig, at atmospheric pressure, or at a sub-atmospheric pressure.

Aspect 6. The process defined in any one of the preceding aspects, wherein the melamine is characterized by any suitable median particle size (d50), or a median particle size (d50) in any range disclosed herein, e.g., from about 10 to about 150 μm, from about 20 to about 120 μm, or from about 40 to about 110 μm.

Aspect 7. The process defined in any one of the preceding aspects, wherein the melamine is characterized by any suitable d90 particle size, or a d90 particle size in any range disclosed herein, e.g., from about 70 to about 250 μm, from about 80 to about 200 μm, or from about 90 to about 175 μm.

Aspect 8. The process defined in any one of aspects 1-7, wherein the molybdenum trioxide is contacted with an aqueous mixture of the melamine.

Aspect 9. The process defined in any one of aspects 1-7, wherein the melamine is contacted with an aqueous slurry of the molybdenum trioxide.

Aspect 10. The process defined in any one of aspects 1-9, wherein the process comprises adding an aqueous mixture of the melamine to a saturated aqueous mixture (solution/slurry) of the molybdenum trioxide having a pH of less than or equal to about 4.

Aspect 11. The process defined in aspect 10, wherein the pH of the saturated aqueous mixture is in any suitable range, or in any range disclosed herein, e.g., from about 1 to about 4, from about 2 to about 4, from about 3 to about 4, from about 1.5 to 4, from about 1.5 to about 3.5, from about 1 to about 3, from about 1.5 to about 2.5, or from about 2 to about 3.

Aspect 12. The process defined in aspect 10 or 11, wherein the aqueous mixture of the melamine is added slowly over any suitable time period, or a time period in any range disclosed herein, e.g., from about 30 min to about 24 hr, from about 1 hr to about 12 hr, or from about 90 min to about 6 hr.

Aspect 13. The process defined in any one of the preceding aspects, wherein the molybdenum trioxide is characterized by any suitable median particle size (d50), or a median particle size (d50) in any range disclosed herein, e.g., from about 0.5 to about 20 µm, from about 1 to about 10 µm, or from about 1.6 to about 6 µm.

Aspect 14. The process defined in any one of the preceding aspects, wherein the molar yield of the melamine octamolybdate, based on the limiting reactant, is in any range disclosed herein, e.g., from about 90 to 100%, from about 95 to 100%, or from about 92 to about 99%.

Aspect 15. The process defined in any one of the preceding aspects, further comprising a step of removing the melamine octamolybdate from the slurry using any suitable technique, or any technique disclosed herein, e.g., filtration or centrifugation, as well as combinations thereof.

Aspect 16. The process defined in any one of the preceding aspects, further comprising a step of drying the melamine octamolybdate under any suitable drying conditions, or any drying conditions disclosed herein, e.g., a drying temperature in a range from about 50° C. to about 200° C., or from about 100° C. to about 150° C., and drying at atmospheric pressure or sub-atmospheric pressure, e.g., less than about 150 Torr, or less than about 50 Torr.

Aspect 17. The process defined in any one of the preceding aspects, wherein the process comprises contacting or reacting the melamine and the molybdenum trioxide in the presence of a core material.

Aspect 18. The process defined in aspect 17, wherein the core material comprises any suitable core material, or any core material disclosed herein, e.g., silica, alumina, alumina trihydrate, talc, calcium carbonate, clay, zinc oxide, zinc borate, or calcium borate, as well as combinations thereof.

Aspect 19. Melamine octamolybdate produced by the process defined in any one of aspects 1-16.

Aspect 20. Melamine octamolybdate characterized by a decomposition onset temperature (or a temperature at a weight loss of 1%, or a temperature at a weight loss of 2%) on a TGA (thermogravimetric analysis) curve in a range from about 300° C. to about 500° C.

Aspect 21. The process or melamine octamolybdate defined in any one of aspects 1-16 or 19-20, wherein the melamine octamolybdate is characterized by any suitable median particle size (d50), or a median particle size (d50) in any range disclosed herein, e.g., from about 0.5 to about 20 µm, from about 1 to about 10 µm, or from about 2 to about 4 µm.

Aspect 22. The process or melamine octamolybdate defined in any one of aspects 1-16 or 19-21, wherein the melamine octamolybdate is characterized by a decomposition onset temperature (or a temperature at a weight loss of 1%, or a temperature at a weight loss of 2%) on a TGA (thermogravimetric analysis) curve in any range disclosed herein, e.g., from about 325° C. to about 475° C., from about 325° C. to about 425° C., or from about 350° C. to about 390° C.

Aspect 23. A supported melamine octamolybdate produced by the process defined in any one of aspects 17-18.

Aspect 24. A supported melamine octamolybdate comprising a melamine octamolybdate supported on a core material, wherein:

the supported melamine octamolybdate is characterized by a decomposition onset temperature (or a temperature at a weight loss of 1%, or a temperature at a weight loss of 2%) on a TGA (thermogravimetric analysis) curve in a range from about 300° C. to about 500° C.; and the core material comprises any suitable core material, or any core material disclosed herein, e.g., silica, alumina, alumina trihydrate, talc, calcium carbonate, clay, zinc oxide, zinc borate, or calcium borate, as well as combinations thereof.

Aspect 25. The process or supported melamine octamolybdate defined in any one of aspects 17-18 or 23-24, wherein the supported melamine octamolybdate is characterized by a decomposition onset temperature (or a temperature at a weight loss of 1%, or a temperature at a weight loss of 2%) on a TGA (thermogravimetric analysis) curve in any range disclosed herein, e.g., from about 325° C. to about 475° C., from about 325° C. to about 425° C., or from about 350° C. to about 390° C.

Aspect 26. A polymer composition (or formulation, or composite) comprising:
(a) a polymer; and
(b) the melamine octamolybdate defined in any one of aspects 19-22 (or the supported melamine octamolybdate defined in any one of aspects 23-25).

Aspect 27. The polymer composition defined in aspect 26, wherein the weight ratio of polymer:melamine octamolybdate (or supported melamine octamolybdate) is any suitable weight ratio, or a weight ratio in any range disclosed herein, e.g., from about 100:1 to about 100:40, from about 100:1 to about 100:5, from about 100:5 to about 100:40, or from about 100:5 to about 100:20.

Aspect 28. The polymer composition defined in aspect 26 or 27, wherein the polymer comprises any suitable polymer, or any polymer disclosed herein, e.g., a thermoplastic, a thermoset, or a combination thereof.

Aspect 29. The polymer composition defined in aspect 26 or 27, wherein the polymer comprises a polyvinylidene chloride (PVDC), a polyvinyl chloride (PVC), a chlorinated polyvinyl chloride (CPVC), a polyvinylidene fluoride (PVDF), a polytetrafluoroethylene (PTFE), an ethylene chlorotrifluoroethylene (ECTFE), or any combination thereof.

Aspect 30. The polymer composition defined in aspect 26 or 27, wherein the polymer comprises a rigid PVC.

Aspect 31. The polymer composition defined in aspect 26 or 27, wherein the polymer comprises a flexible PVC.

Aspect 32. The polymer composition defined in aspect 26 or 27, wherein the polymer comprises a plasticized or non-plasticized PVC.

Aspect 33. The polymer composition defined in any one of aspects 26-32, where the polymer composition further comprises an inorganic flame retardant, e.g., aluminum trihydrate or magnesium hydroxide, as well as any combination thereof.

Aspect 34. The polymer composition defined in any one of aspects 26-33, wherein the polymer composition has any suitable normalized total smoke, or a normalized total smoke in any range disclosed herein, e.g., from about 30 to about 50, from about 35 to about 50, or from about 35 to about 45, in $m^2/m^2$ per gram of the polymer composition.

Aspect 35. The polymer composition defined in any one of aspects 26-34, wherein the polymer composition has a normalized total smoke that is less than that (or within about 5 m²/m² per gram, or within about 2 m²/m² per gram) of a polymer composition containing ammonium octamolybdate, under the same processing conditions and with the same amount of smoke suppressant.

Aspect 36. The polymer composition defined in any one of aspects 26-35, wherein the polymer composition has a normalized total smoke that is less than that (or within about 5 m²/m² per gram, or within about 2 m²/m² per gram) of a polymer composition containing a zinc molybdate/magnesium hydroxide complex, under the same processing conditions and with the same amount of smoke suppressant.

Aspect 37. An article of manufacture comprising the polymer composition defined in any one of aspects 26-36.

Aspect 38. The article defined in aspect 37, wherein the article comprises a sheet or film.

Aspect 39. The article defined in aspect 37, wherein the article comprises a tube or pipe.

Aspect 40. The article defined in aspect 37, wherein the article comprises a wire or cable.

We claim:

1. A process for producing melamine octamolybdate, the process comprising reacting molybdenum trioxide ($MoO_3$) and melamine in an acidic aqueous system at a pH of less than or equal to about 4 to form a slurry of the melamine octamolybdate; wherein:
    the melamine octamolybdate is characterized by a temperature at a weight loss of 1% on a thermogravimetric analysis curve in a range from about 300° C. to about 500° C.; and/or
    the melamine octamolybdate is characterized by a temperature at a weight loss of 2% on a thermogravimetric analysis curve in a range from about 300° C. to about 500° C.

2. The process of claim 1, wherein the melamine octamolybdate is further characterized by a decomposition onset temperature on a thermogravimetric analysis curve in a range from about 300° C. to about 500° C.

3. The process of claim 1, wherein:
    the pH is in a range from about 1.5 to about 4;
    a Mo:N molar ratio of molybdenum trioxide to melamine is in a range from about 1:2 to about 2:7, based on the total amount of each reactant; and
    the slurry of the melamine octamolybdate is formed at a temperature in a range from about 70° C. to about 95° C.

4. The process of claim 1, wherein:
    a molar yield of the melamine octamolybdate, based on the limiting reactant, is in a range from about 90 to 100%;
    the melamine has a d50 particle size in a range from about 10 to about 150 μm;
    the molybdenum trioxide has a d50 particle size in a range from about 0.5 to about 20 μm; and
    the melamine octamolybdate has a d50 particle size is a range from about 0.5 to about 20 μm.

5. The process of claim 1, wherein reacting molybdenum trioxide and melamine in the acidic aqueous system comprises:
    contacting an aqueous slurry of the molybdenum trioxide with an aqueous mixture of the melamine.

6. The process of claim 1, wherein reacting molybdenum trioxide and melamine in the acidic aqueous system comprises:
    adding an aqueous mixture of the melamine to a saturated aqueous mixture of the molybdenum trioxide having a pH in a range from about 2 to about 4;
    wherein the acidic aqueous system, after adding the aqueous mixture of the melamine, has a pH in a range from about 2 to about 4.

7. The process of claim 1, wherein:
    the melamine octamolybdate is characterized by a temperature at a weight loss of 1% on a thermogravimetric analysis curve in a range from about 330° C. to about 400° C.; and/or
    the melamine octamolybdate is characterized by a temperature at a weight loss of 2% on a thermogravimetric analysis curve in a range from about 350° C. to about 390° C.

8. The process of claim 1, wherein the process further comprises:
    a step of removing the melamine octamolybdate from the slurry via filtration and/or centrifugation; and
    a step of drying the melamine octamolybdate.

9. A melamine octamolybdate produced by the process of claim 1.

10. The process of claim 1, wherein the slurry of the melamine octamolybdate is formed in the presence of a core material comprising, silica, alumina, alumina trihydrate, talc, calcium carbonate, clay, zinc oxide, zinc borate, calcium borate, or any combination thereof.

11. A supported melamine octamolybdate produced by the process of claim 10.

12. The process of claim 1, wherein the pH is in a range from about 1.5 to about 3.5.

13. The process of claim 12, wherein:
    the melamine octamolybdate is characterized by a temperature at a weight loss of 1% on a thermogravimetric analysis curve in a range from about 330° C. to about 400° C.; and/or
    the melamine octamolybdate is characterized by a temperature at a weight loss of 2% on a thermogravimetric analysis curve in a range from about 330° C. to about 400° C.

14. The process of claim 12, wherein reacting molybdenum trioxide and melamine in the acidic aqueous system comprises:
    contacting an aqueous slurry of the molybdenum trioxide with an aqueous mixture of the melamine.

15. The process of claim 12, wherein the slurry of the melamine octamolybdate is formed in the presence of a core material comprising, silica, alumina, alumina trihydrate, talc, calcium carbonate, clay, zinc oxide, zinc borate, calcium borate, or any combination thereof.

16. The process of claim 12, wherein a Mo:N molar ratio of molybdenum trioxide to melamine is in a range from about 1:2 to about 2:7, based on the total amount of each reactant.

17. The process of claim 1, wherein the pH is in a range from about 1 to about 4.

18. The process of claim 17, wherein:
    the melamine has a d50 particle size in a range from about 40 to about 110 μm; and
    the melamine octamolybdate has a d50 particle size is a range from about 1 to about 10 μm.

19. The process of claim 1, wherein reacting molybdenum trioxide and melamine in the acidic aqueous system comprises:
    adding an aqueous mixture of the melamine to a saturated aqueous mixture of the molybdenum trioxide having a pH in a range from about 1 to about 4;

wherein the acidic aqueous system, after adding the aqueous mixture of the melamine, has a pH in a range from about 1 to about 4.

20. The process of claim 1, wherein reacting molybdenum trioxide and melamine in the acidic aqueous system comprises:

adding an aqueous mixture of the melamine to a saturated aqueous mixture of the molybdenum trioxide having a pH in a range from about 1.5 to about 3.5;

wherein the acidic aqueous system, after adding the aqueous mixture of the melamine, has a pH in a range from about 1.5 to about 3.5.

* * * * *